(12) United States Patent
Engel et al.

(10) Patent No.: US 12,243,644 B2
(45) Date of Patent: Mar. 4, 2025

(54) MEDICAL DIAGNOSIS ASSISTANCE SYSTEM AND METHOD

(71) Applicant: Siemens Healthcare Diagnostics Inc., Tarrytown, NY (US)

(72) Inventors: Thomas Engel, Aalen (DE); Gaby Marquardt, Hausen (DE); Jens-Peter Brock, Langenzenn (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 420 days.

(21) Appl. No.: 17/868,605

(22) Filed: Jul. 19, 2022

(65) Prior Publication Data

US 2023/0025181 A1 Jan. 26, 2023

(30) Foreign Application Priority Data

Jul. 20, 2021 (EP) .................................... 21186626

(51) Int. Cl.
*G16H 30/40* (2018.01)
*G06T 7/00* (2017.01)
*G16H 50/20* (2018.01)

(52) U.S. Cl.
CPC .......... *G16H 50/20* (2018.01); *G06T 7/0012* (2013.01); *G16H 30/40* (2018.01); *G06T 2207/20081* (2013.01); *G06T 2207/30024* (2013.01)

(58) Field of Classification Search
CPC ........ G16H 50/20; G16H 30/40; G16H 10/40; G16H 50/70; G06T 7/0012; G06T 2207/20081; G06T 2207/30024; Y02A 90/10; G06F 18/2148; G06F 18/2413;
(Continued)

(56) References Cited

U.S. PATENT DOCUMENTS 9,739,783 B1 * 8/2017 Kumar ............ G01N 33/57449
11,594,403 B1 * 2/2023 Steingrimsson ....... G16H 50/20
11,978,198 B2 * 5/2024 Ohsaka .................. G16H 30/40
(Continued)

OTHER PUBLICATIONS

Kassim, Y. et al.: Clustering-Based Dual Deep Learning Architecture for Detecting Red Blood Cells in Malaria Diagnostic Smears. IEEE Journal of Biomedical and Health Informatics, Piscataway, NJ, USA; vol. 25, No. 5; Oct. 29, 2020 (Oct. 29, 2020); pp. 1735-1746; XP011853832; ISSN: 2168-2194; DOI:10.1109/JBHI.2020.3034863.
(Continued)

*Primary Examiner* — Cindy Trandai
(74) *Attorney, Agent, or Firm* — Dugan & Dugan, PC (57) ABSTRACT

A medical diagnosis assistance system, a medical diagnosis assistance method, and a training method for training an artificial intelligence entity are disclosed. The medical diagnosis assistance system includes: an input interface configured to receive medical image data of a patient; a computing device configured to implement: a classification module configured to classify parts of interest, POI, comprising objects of interest, OOI, and/or regions of interest, ROI, within the received medical image data, and to assign a corresponding reliability metric to each of the classified POI; and an analysis module configured to determine, based on the POI and the assigned reliability metric, an analysis of the medical image data; and an output interface configured to output an output signal indicating the analysis.

13 Claims, 4 Drawing Sheets

(58) Field of Classification Search
CPC ...... G06V 10/25; G06V 20/698; G06V 10/82; G06N 3/08; G06N 20/20; G06N 20/00
See application file for complete search history.

(56) References Cited

U.S. PATENT DOCUMENTS

| | | | | |
|---|---|---|---|---|
| 11,983,612 | B2* | 5/2024 | Kuwamori | G06F 16/55 |
| 2006/0039593 | A1* | 2/2006 | Sammak | G06V 10/764 |
| | | | | 382/160 |
| 2008/0063265 | A1* | 3/2008 | Sathyanarayana | G06F 18/211 |
| | | | | 382/159 |
| 2015/0102216 | A1* | 4/2015 | Roder | G06V 20/698 |
| | | | | 250/281 |
| 2017/0053211 | A1* | 2/2017 | Heo | G06N 20/00 |
| 2017/0132450 | A1* | 5/2017 | El-Zehiry | G06T 7/0012 |
| 2017/0212028 | A1* | 7/2017 | Correia De Matos Nolasco Lamas | G01N 15/1436 |
| 2017/0270666 | A1* | 9/2017 | Barnes | G01N 33/57415 |
| 2018/0285731 | A1* | 10/2018 | Heifets | G06N 3/04 |
| 2018/0322660 | A1* | 11/2018 | Smith | G06T 7/97 |
| 2020/0049599 | A1* | 2/2020 | Alexander | G01N 33/5091 |
| 2020/0160032 | A1* | 5/2020 | Allen | G16H 50/30 |
| 2020/0191643 | A1* | 6/2020 | Davis | G01H 1/00 |
| 2020/0340909 | A1* | 10/2020 | Ohsaka | G01N 15/1433 |
| 2021/0020310 | A1* | 1/2021 | Kikuchi | G06F 16/906 |
| 2021/0163313 | A1* | 6/2021 | Arndt | C02F 3/006 |
| 2023/0177699 | A1* | 6/2023 | Ray | G06V 10/82 |
| | | | | 382/173 |
| 2023/0260111 | A1* | 8/2023 | Rodrigues-Diaz | G06T 7/0012 |
| | | | | 382/128 |

OTHER PUBLICATIONS

Raina S., et al.: "Blood Cells Detection 1-11 Using Faster-RCNN"; 2020 IEEE International Conference on Computing, Power and Communication Technologies (GUCON), IEEE; Oct. 2, 2020 (Oct. 2, 2020); pp. 217-222; XP033847723; DOI: 10.1109/GUCON48875.2020.9231134.

Yang, F et al.: "Cascading YOLO: Automated Malaria Parasite Detection for Plasmodium Vivax in Thin Blood Smears"; Proc. SPIE 11314, Medical Imaging 2020: Computer-Aided Diagnosis, 113141Q (Mar. 16, 2020); https://doi.org/10.1117/12.2549701.

* cited by examiner

MEDICAL DIAGNOSIS ASSISTANCE SYSTEM AND METHOD

CROSS REFERENCE TO RELATED APPLICATION

This claims priority to European Patent Application No. EP 21186626.4, filed Jul. 20, 2021, which is hereby incorporated by reference herein in its entirety for all purposes.

FIELD OF THE INVENTION

The present invention relates to a medical diagnosis assistance system as well as to a medical diagnosis assistance method. Moreover, a method for training an artificial intelligence entity for use in the system and/or in the method is provided. In some cases, the system or the method may automatically provide a diagnosis. In these cases, the system may also be designated as a medical diagnosis system, and the method may be designated as a medical diagnosis method.

Although applicable for any type of medical diagnosis assistance, in particular, applications in Hematology and Pathology are described.

BACKGROUND OF THE INVENTION

Artificial intelligence (AI) based systems for analyzing medical data are coming up in great number based on various data analysis methods from principal component analysis (PCA), partial least squares (PLS), convolutional neural networks (CNN), deep CNN, artificial intelligence (AI), machine learning (ML), or computer learning (CL). All these methods are subsumed under terms "artificial intelligence entity" in the present disclosure.

In medical diagnosis, usually there are highly relevant and specific markers for a specific disease and related diagnosis. For example, in the case of Hematology and acute leukemia (AML), cells with so called Auer rods are a direct proof of the AML diagnosis.

However, in a particular patient, the actual occurrence of such Auer rods may be, in a beginning stage, relatively scarce. Human physicians must, by the limitations imposed upon them by time, cost, and the realities of the human body, restrict themselves to investigating a select few samples which limits the human physicians' chances of successfully diagnosing AML on the basis of the occurrence of Auer rods.

On the other hand, human physicians have a remarkable capability of evaluating the entire context of any given sample and to draw conclusions therefrom. Usually, they are also able to give convincing reasoning for their diagnosis to a colleague or the patient in a report such that they are universally awarded a high degree of trust. By contrast, artificial intelligence entities often function as a "black box" which may provide superior results whereas the exact reasoning how the result was achieved remains opaque. In some extreme cases, the effort of verifying or corroborating the result by such a "black box" artificial intelligence entity may even equal the effort to produce the result by a human physician in the first place.

SUMMARY OF THE INVENTION

An objective of the present invention is solving the problems posed by the situation described above. The object is solved by the subject-matter of the independent claims. The dependent claims provide embodiments, refinements, or variants of embodiments, of the basic ideas or aspects of the present invention.

Accordingly, a medical diagnosis assistance system comprises:
an input interface configured to receive medical image data of a patient;
a computing device configured to implement:
a classification module configured to classify parts of interest, POI, comprising objects of interest, OOI, and/or regions of interest, ROI, within the received medical image data, and to assign a corresponding reliability metric to each of the classified POI; and
an analysis module configured to determine, based on the POI and the assigned reliability metric, analysis of the medical image data; and
an output interface configured to output an output signal indicating the analysis.

Both the input interface and/or the output interface may be realized in hardware and/or software, cable-bound and/or wireless, and in any combination thereof. Any of the interfaces may comprise an interface to an intranet or the Internet, to a cloud computing service, to a remote server, and/or the like.

The computing device may be realised as any device, or any means, for computing, in particular, for executing software, an app, or an algorithm. For example, the computing device may comprise at least one processing unit such as at least one central processing unit, CPU, and/or at least one graphics processing unit, GPU, and/or at least one field-programmable gate array, FPGA, and/or at least one application-specific integrated circuit, ASIC, and/or any combination of the foregoing. The computing device may further comprise a working memory operatively connected to the at least one processing unit and/or a non-transitory memory operatively connected to the at least one processing unit and/or the working memory. The computing device may be implemented partially and/or completely in a local apparatus and/or partially and/or completely in a remote system such as by a cloud computing platform.

Any or all of the modules, in particular, the classification module and/or the analysis module, may be implemented as software and/or hardware.

In systems based on cloud computing technology, a large number of devices is connected to a cloud computing system via the Internet. The devices may be located in a remote facility connected to the cloud computing system. For example, the devices can comprise, or consist of, equipment, sensors, actuators, robots, and/or machinery in an industrial set-up(s). The devices can be medical devices and equipment in a healthcare unit. The devices can be home appliances or office appliances in a residential/commercial establishment.

The cloud computing system may enable remote configuring, monitoring, controlling, and maintaining connected devices (also commonly known as 'assets'). Also, the cloud computing system may facilitate storing large amounts of data periodically gathered from the devices, analyzing the large amounts of data, and providing insights (e.g., key performance indicators, outliers) and alerts to operators, field engineers, or owners of the devices via a graphical user interface (e.g., of web applications). The insights and alerts may enable controlling and maintaining the devices, leading to efficient and fail-safe operation of the devices. The cloud computing system may also enable modifying parameters associated with the devices and issues control commands via the graphical user interface based on the insights and alerts.

The cloud computing system may comprise a plurality of servers or processors (also known as 'cloud infrastructure'), which are geographically distributed and connected to each other via a network. A dedicated platform (hereinafter referred to as a 'cloud computing platform') is installed on the servers/processors for providing the above functionality as a service (hereinafter referred to as a 'cloud service'). The cloud computing platform may comprise a plurality of software programs executed on one or more servers or processors of the cloud computing system to enable delivery of the requested service to the devices and its users.

One or more application programming interfaces (APIs) are deployed in the cloud computing system to deliver various cloud services to the users.

A part of interest, POI, may be any or all of:
an object of interest, OOI, in particular an object depicted and identified in the medical image data, more specifically such an object which also has been deemed to be "of interest" according to a pre-defined metric;
a region of interest, ROI;
an area of interest, AOI; and/or
any other type of data subset of interest, DSOI.

In the field of Hematology, for example, objects of interest, OOI, will typically be cells within a blood sample.

The reliability metric may, for example, be a percentage indicating the confidence of the classification module in its own classification. If the uncertainty for a classification is calculated or is available for the reliability metric, a trust level can be calculated according to a given model which might be domain specific or simply by calculating: "trust level=1−uncertainty". The reliability metric may also either be a percentage level that the classification module in operation outputs for the respective data set or subset of data analysed. More preferably, the reliability metric is produced by a more sophisticated approach by independent analytical tools for the quality of classification or output generated by KPI or trust levels. Whenever the reliability metric is mentioned herein, it shall be understood that this may be a numerical value indicating a reliability or trust or, respectively, lack thereof (e.g., uncertainty).

An analysis (or: medical analysis, or pre-diagnosis), as the term is used herein, may comprise a diagnosis, i.e., an indication that a specific disease or condition may be (or even: is) present (with or without a corresponding degree of certainty), an indication that a specific test should be performed, an indication that a specific workflow should be started, a graphical overview of the classification performed by the classification module, and/or the like.

One main idea of the present application is that a computer-implemented medical diagnosis assistance is not limited by the same constraints as a human physician (or a trained biologist or the like) while on the other hand it can be designed such as to emulate, or simulate, the decision-making by a human physician. Advantageously, a multi-step approach from data capture all the way down to a solid diagnosis is provided.

In some advantageous embodiments, refinements, or variants of embodiments, the classification module is configured to implement a classifying artificial intelligence entity, CAIE, which is trained and configured to receive at least a portion of the received medical image data and to generate, based thereon, a classifying artificial intelligence entity output classifying the part of interest, POI, and/or the corresponding reliability metric. Preferably, the entire medical image data are provided to the classifying artificial intelligence entity, CAIE. The classifying artificial intelligence entity, CAIE, output may be a vector, or a matrix, of entries indicating the part of interest, POI, and/or the reliability metric.

Whenever herein an artificial intelligence entity is mentioned, it shall be understood that this may comprise, or consist of, principal component analysis (PCA), partial least squares (PLS), artificial neural networks (ANN), in particular convolutional neural networks (CNN), deep CNN, artificial intelligence (AI), machine learning (ML), or computer learning (CL) algorithms or constructs. Preferably, artificial neural networks (ANN) and in particular convolutional neural networks, CNN, are used, which have been used with great success in all areas of automated image processing.

In some advantageous embodiments, refinements, or variants of embodiments, a two-part classification scheme is employed, in which: the AIE comprises a first-level classifying artificial intelligence sub-entity, FLCAISE, and a second-level artificial intelligence sub-entity, SLCAISE.

The first-level classifying artificial intelligence sub-entity, FLCAISE, may be trained and configured to receive, as its input, at least a portion (or all of) of the received medical image data and to generate, based thereon, a first-level classifying artificial intelligence sub-entity, FLCAISE, output classifying the POI according to a broad classification scheme.

The second-level artificial intelligence sub-entity, SLCAISE, may be trained and configured to receive, as its input, at least a portion (or all of) of the received medical image data and the first-level classifying artificial intelligence sub-entity, FLCAISE, output, and to further classify the part of interest, POI, according to a refined classification scheme.

In this context, "broad" and "refined" may be considered to be dependent on one another, in that the "broad classification" is broader than the "refined classification," and the "refined classification" is more detailed, or more refined, than the "broad classification." Expressed in another way, the broad classification defines types, and the refined classification defines sub-types. Preferably, the refined classification provides at least two sub-types for at least one type according to the broad classification (e.g., at least two different sub-types of white blood cells for the type "white blood cell").

Thus, each part of interest, POI, may, after the refined classification by the second-level artificial intelligence sub-entity, SLCAISE, be labelled with each of a type (according to the broad classification by the first-level classifying artificial intelligence sub-entity, FLCAISE) and a sub-type (according to the refined classification by the second-level artificial intelligence sub-entity, SLCAISE). In the presentation of the analysis to a human user (e.g., a human physician), this label may be used to hide or show certain data, or to provide a user with a desired level of detail (e.g., type-level detail or sub-type-level detail).

This two-part classification scheme emulates or simulates the process of human physicians. For example, in the medical field of Hematology in the case of medical image data, often are magnified visual images of samples. Human physicians typically first determine a blood component type, i.e., whether an object within an image is, for example, a white blood cell (or: leucocyte, leukocyte, or WBC), or a red blood cell (or: erythrocyte, or red cell), or a platelet (or: thrombocyte). Then, e.g., the human physicians focus on the white blood cells and determine their individual sub-types. The presence or lack of certain blood component types or blood component sub-types may already give rise to some diagnoses or rule out others.

Thus, the broad classification scheme may relate to types, and the refined classification scheme to sub-types (if existent) within these types. The type "white blood cell," for example, may be defined to comprise the sub-types of "neutrophile granulocyte," "lymphocyte," "monocyte," "eosinophile granulocyte," and "basophile granulocyte."

Each classification scheme, be it "broad" or "refined," may comprise a classification for the background and/or a "fallback classification" into which parts of interest, POI, are classified which are not background but which cannot be accurately classified at the time. Such a "fallback classification" may be designated "rest" or "unclear" or the like. In some variants of embodiments, at least one iteration loop is performed such that POIs classified into "unclear" can advantageously be re-classified into other classifications based on new information, such as a (first) analysis of the medical image data.

In some advantageous embodiments, refinements, or variants of embodiments, the classification module comprises a cropping sub-module, CSM, configured to receive the first-level classifying artificial intelligence sub-entity, FLCAISE, output and to generate excerpts from the received medical image data, each excerpt associated with a single POI and comprising at least the corresponding associated POI, and to provide the generated excerpts to the SLCAISE as the input of the SLCAISE. Preferably, both a part of interest, POI, currently under scrutiny (or analysis) is included in the excerpts as well as a predefined area of the medical image data surrounding the part of interest, POI. In this manner, the surroundings can be taken into account for the analysis.

Each step, in particular, the classification into the broad classification scheme and/or the classification into the refined classification scheme may be performed once or more than once. In between, image processing steps such as cropping, stitching, and the like on the medical image data may be performed.

In an exemplary workflow, medical image data are generated and optionally stitched together in order to form larger images or to connect seams. Then, an object detection may be performed (to detect parts of interest, POI) which may already provide a first classification into a broad classification scheme. After the object detection, the images may be cropped around each detected POI, and a second classification into a refined classification scheme may be performed. Then, the analysis may be provided based on the refined classifications and at least a part of the croppings.

Alternatively, the cropping may be performed first, then one or more first classifications into one or more broad classification schemes is performed, and then one or more second classifications into one or more refined classification schemes is performed. The result of each classification step may be used as input for a following classification step and/or for an iterative improvement of a previous classification step.

In some advantageous embodiments, refinements, or variants of embodiments, the analysis module is configured to implement an analyzing artificial intelligence entity, AAIE, which is trained and configured to receive, as its input, the classified POI and the assigned reliability metric and to generate, based thereon, the analysis (e.g., a diagnosis). Alternatively, or additionally, the analysis module may comprise one or more decision rules, pattern analysis sub-modules, and/or the like in order to generate the analysis. In this way, additional medical knowledge can be taken into account for the analysis, for example, medical decision rules present in textbooks such as "presence of at least one Auer rod" (e.g., object has class "white blood cell," subtype "white blood cell with Auer rod")→analysis: "diagnosis of AML."

In some advantageous embodiments, refinements, or variants of embodiments, the analysis module and the classification module are configured to perform at least one refinement loop. Each refinement loop may be defined as comprising:
  a) generating, by the analysis module, a preliminary analysis, preferably automatically or involving an input by a user;
  b) receiving, by the classification module, the preliminary analysis by the analysis module and re-classifying the POI and/or re-assigning the corresponding reliability metric based on the preliminary analysis, and
  c) determining, based on the re-classified POI and/or the re-assigned corresponding reliability metric, another preliminary analysis.

After the last refinement loop the preliminary analysis is used (or: provided) as the analysis of the analyzing module. In this way, findings in the analysis may be used to re-evaluate and confirm, or overturn, the previous classification.

In some advantageous embodiments, refinements, or variants of embodiments, the input interface is configured to receive medical image data comprising at least 20 (preferably at least 100, more preferably at least 500, most preferably at least 1000) parts of interest, POI, to be classified, and wherein the classification module is configured to classify at least 20 (preferably at least 100, more preferably at least 500, most preferably at least 1000) of the at least 20 (preferably at least 100, more preferably at least 500, most preferably at least 1000) parts of interest, POI, comprised in the medical image data. Such parts of interest, POI, may for example be individual blood cells. By treating such numbers of parts of interest, POI, the system easily surpasses the capabilities of a human physician, in particular, when the classification and/or the analysis is based on all of the parts of interest, POI, and when the individual classification of each part of interest, POI, may depend on a plurality, or even all of, the classifications of the other parts of interest, POI.

In Hematology applications, for example, blood samples usually comprise a high number of blood components from which only an excerpt is typically presented to human physicians which then may perform further selections from that selection. By contrast, the present system may classify and analyze based on all available blood components (in particular blood cells) in the blood sample. In this way, the facts and resources at hand are maximally exploited in order to produce the best possible analysis, and preferably diagnosis.

In some advantageous embodiments, refinements, or variants of embodiments, the medical image data are magnified visual images of blood samples, and the parts of interest, POI, comprise blood components (in particular: blood cells) within the blood samples as objects of interest, OOI. The visual images may be dyed, or undyed, or may comprise both dyed and undyed visual images. Of course, blood samples are, when they are taken, undyed, and may then be optically scanned in order to produce undyed magnified visual images. Thereafter, the blood samples may be dyed and optically scanned again, in order to produce dyed magnified visual images.

Human physicians typically work with dyed blood samples, in which, for example, regular white blood cells take on some amount of blue color. Dyed samples may provide some very distinctive results regarding some conditions so that it may be advantageous to use magnified visual images of dyed samples as medical image data. Correspondingly, such magnified visual images, together with corresponding labels (e.g., ground truths determined by a human physician or biologist or the like) may also be used for training one or more of the artificial intelligence entities described herein using supervised training, semi-supervised training, or unsupervised training.

However, dying samples may also introduce some elements of confusion, for example, in rare cases where a red blood cell takes on blue dye. Too-simply trained artificial intelligence entities may have learned to identify blue dying and to classify objects with blue dye directly as white blood cells. Thus, training artificial intelligence entities additionally, or alternatively, with undyed samples forces the artificial intelligence entities to focus more on shapes and patterns and the like. As a possible additional or alternative type of training samples and/or input medical image data, de-colored dyed images, i.e., images of dyed samples which have been transformed into grayscale images, may be used. In such images, the patterns created by the dye are preserved but the additional information about the color itself is removed.

Instead of visual images, other images may be provided as the medical image data, for example, images taken by any medical imaging device.

The invention further provides a computer-implemented medical diagnosis assistance method, comprising at least the steps of:

receiving medical image data of a patient;

classifying parts of interest, POI, comprising objects of interest, OOI, and/or regions of interest, ROI, within the received medical image data;

assigning a corresponding reliability metric to each of the classified part of interest, POI; and determining, based on the POI and the assigned reliability metric, an analysis of the medical image data.

It shall be understood that the method according to the present invention may be performed by the system according to the present invention. Therefore, any embodiment of the method according to the present invention may be adapted, modified, or refined according to any of the variants, options, modifications, or refinements of any of the embodiments of the system according to the present invention.

In some advantageous embodiments, refinements, or variants of embodiments, the method further comprises steps of:

generating, using a trained first-level classifying artificial intelligence sub-entity, FLCAISE, a first-level classifying artificial intelligence sub-entity FLCAISE output classifying at least a part of the parts of interest, POI, according to a broad classification scheme, based on at least a portion of the received medical image data; and generating, using a trained second-level classifying artificial intelligence sub-entity, SLCAISE, a second-level classifying artificial intelligence sub-entity, SLCAISE, output classifying the at least part of the part of interest, POI, according to a refined classification scheme, based on at least a portion of the received medical image data (which may be the same portion as the one for the FLCAISE or a different portion) and on the first-level classifying artificial intelligence, FCLAISE, sub-entity output.

The advantages of this two-step analysis, or two-tiered approach, have already been extolled in the foregoing.

In some advantageous embodiments, refinements, or variants of embodiments, the method further comprises steps of:

generating excerpts from the received medical image data, each excerpt associated with a single POI and comprising at least the corresponding associated POI, and providing the generated excerpts to the SLCAISE as the input of the SLCAISE.

The invention further provides a computer-implemented training method for training a classifying artificial intelligence entity, CAIE, comprising at least the steps of:

providing first labelled samples of medical image data;

providing a first-level classifying artificial intelligence sub-entity, FLCAISE, in a preliminary state;

performing supervised learning, using the first labelled samples, in order to train the first-level classifying artificial intelligence sub-entity, FLCAISE, to classify parts of interest, POI, within an input of the first-level classifying artificial intelligence sub-entity, FLCAISE, according to a broad classification scheme;

providing second labelled samples of medical image data;

providing a second-level artificial intelligence sub-entity, SLCAISE, in a preliminary state;

performing supervised learning, using the second labelled samples, in order to train second-level artificial intelligence sub-entity, SLCAISE, to classify parts of interest, POI, within an input of the second-level classifying artificial intelligence sub-entity, SLCAISE, according to a refined classification scheme; and providing a trained classifying artificial intelligence entity, CAIE, comprising both the trained first-level classifying artificial intelligence sub-entity, FLCAISE, and the trained second-level artificial intelligence sub-entity, SLCAISE.

Artificial neural networks, especially convolutional neural networks, are preferred for the first-level classifying artificial intelligence sub-entity, FLCAISE, and the second-level artificial intelligence sub-entity, SLCAISE. Their respective preliminary state may be a state in which all parameters (e.g., weights and biases) are randomized, or set to some specific starting values, for example, after a pre-training has been performed.

The trained classifying artificial intelligence entity, CAIE, may be employed in any method or any system according to the present invention. Moreover, the steps of training the first-level classifying artificial intelligence sub-entity, FLCAISE, and the steps of training the second-level artificial intelligence sub-entity, SLCAISE, may also be performed independently from one another, and even without the respective other steps being performed at all. The training method may thus be also used to provide a trained first-level classifying artificial intelligence sub-entity, FLCAISE, and/or a trained second-level artificial intelligence sub-entity, SLCAISE.

It shall be understood that training may be done in a supervised manner as described above, in a semi-supervised manner or even in an unsupervised manner.

In a preferred embodiment of the training method for training an artificial intelligence entity, AIE, data sets for training any of the artificial intelligence entities, AIE, described herein may be enriched with supplementary information on the ensemble of input data for each patient sample set, e.g., by a confirmed diagnosis based on alternative and/or diverse analytics like FACS analytics in Hematology, genome analytics like DNA data of partial or full sequencing or any other method of fine analytics or precision diagnosis, preferably according to standard of care or research methods of choice. By that additional input, the training of especially the classifying artificial intelligence entity, CAIE, has solidified input to the ensemble of data sets/data subsets from a single/individual patient over the whole distribution of different patients.

This enables the training of the classifying artificial intelligence entities, CAIE, over time to evolve new patterns of indicative constellations for given and even new diagnoses based on the most trustworthy classified samples from the classification and the ensemble information for approved diagnosis for a particular disease which may compliment the hard diagnose on highly distinctive classes with low representation like in the AML case. This approach bears the chance to identify more highly decisive patterns in the future even for hard to diagnose diseases. Today's limitations arise in part from the fact that humans are quite limited in detecting underlying (simple) rules in large and confusing data volumes. This approach here can make use of computer network abilities for abstraction on patterns not intuitive for humans and related generalization based on the analysis of large amounts of data.

In many cases, the medical image data comprise a large number of parts of interest, POI, so that they may be quite confusing for a human researcher or physician. The approach described herein can advantageously be performed iteratively, wherein additional information such as patient-specific data, emerging trends, or results from alternative diagnostic approaches can be taken into account. Thus, a broad classification which left a large number (e.g., 30% or so) of parts of interest, POI, in a "rest" (or: "unclear") class of objects that could not be clearly classified, may be repeated after at least one step of a refined classification has been performed, which may be based also on the analysis of the medical image data. This iterative process may be repeated until an analysis or diagnosis with a pre-defined reliability value has been generated.

Thus, although in many cases it may be preferable to have all POIs classified, often it is acceptable if sufficient POIs have been classified to provide an analysis or diagnosis that has been deemed to be sufficiently reliable.

The iterative approach takes into account that some pathologies are difficult to classify separately, so that the results of each classification or analysis step may be used to perform (for example at least one) iteration of any or all previous classification or analysis steps in order to improve upon them.

The iterative approach can be adaptive to the specifics of each patient, or to the specifics of an analysis or diagnosis provided earlier. For example, if a specific diagnosis must, in order to be deemed reliable, absolutely exclude the occurrence of a specific object "X" in the medical image data, then the approach may be iteratively continued until either object "X" has been found and classified, or all objects have been classified without any occurrence of "X," or a break condition has been reached (e.g., a maximum number of iterations is reached, indicating that no further progress is to be expected).

In some advantageous embodiments, refinements, or variants of embodiments, the second labelled samples comprise less parts of interest, POI, than the first labelled samples. This reflects the two-stage approach in which first the general situation is assessed (or analyzed), and then details are taken into account.

In some advantageous embodiments, refinements, or variants of embodiments, the first labelled samples comprise magnified visual images of blood samples wherein blood components (in particular: blood cells), as objects of interest, OOI, are labelled according to blood component types.

In some advantageous embodiments, refinements, or variants of embodiments, the second labelled samples comprise magnified visual images of blood samples wherein components (in particular: blood cells), as objects of interest, OOI, are labelled according to blood component sub-types.

In some advantageous embodiments, refinements, or variants of embodiments, the first labelled samples and/or the second labelled samples comprise magnified visual images of undyed and/or dyed blood samples.

The invention further provides a computer program product comprising executable program code configured to, when executed, perform the medical diagnosis assistance method and/or the training method according to any of the embodiments of the present invention.

The invention also provides a non-transient computer-readable data storage medium comprising executable program code configured to, when executed, perform the medical diagnosis assistance method and/or the training method according to any of the embodiments of the present invention. The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick, or the like.

The invention further provides a data stream comprising, or configured to generate, executable program code configured to, when executed, perform the medical diagnosis assistance method and/or the training method according to any of the embodiments of the present invention.

BRIEF DESCRIPTION OF THE DRAWINGS

The invention will be explained in greater detail with reference to exemplary embodiments depicted in the drawings as appended.

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as they become better understood by reference to the following detailed description. The elements of the drawings are not necessarily to scale relative to each other. Like reference numerals designate corresponding similar parts.

In the figures.

DETAILED DESCRIPTION OF THE INVENTION

Although specific embodiments have been illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

Figure 1:
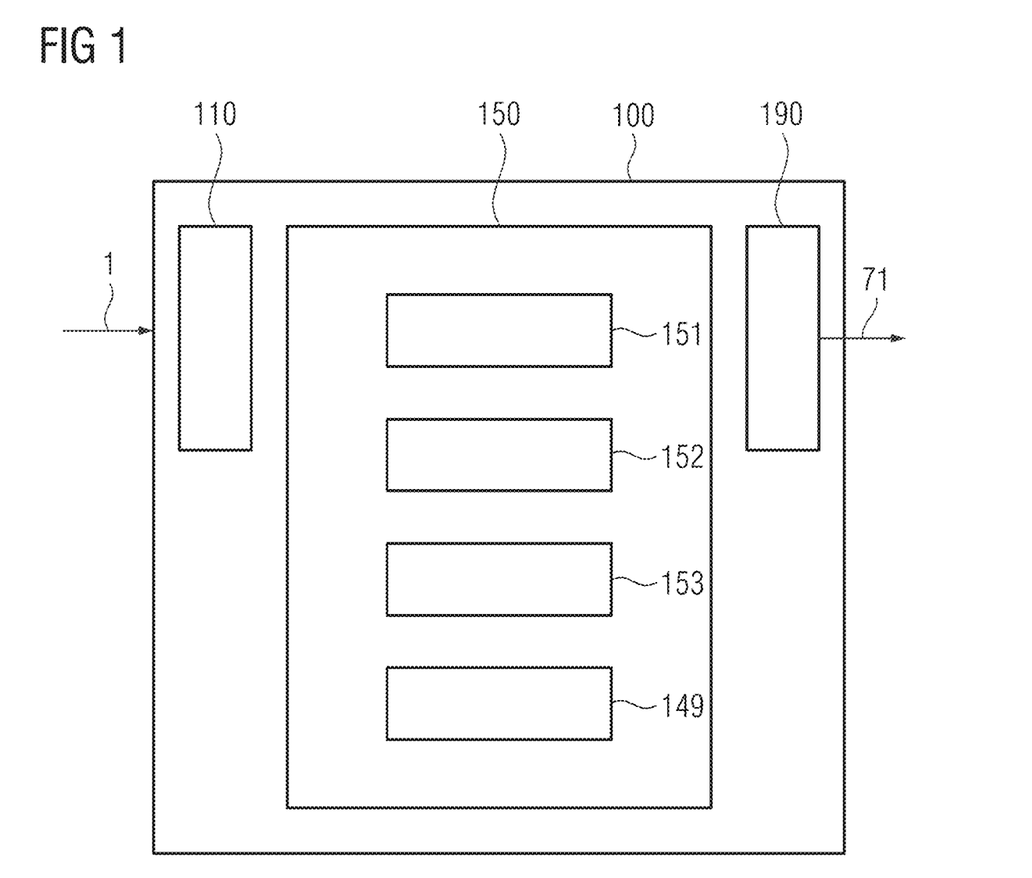
FIG. 1 schematically illustrates a medical diagnosis assistance system according to an embodiment of the present invention.

FIG. 1 schematically illustrates a medical diagnosis assistance system 100 according to an embodiment of the present invention.

The medical diagnosis assistance system 100 comprises an input interface 110 and an output interface 190. As has been described in the foregoing, these interfaces 110, 190 may be realized as hardware and/or software, cable-bound or wireless, between local devices and/or to the Internet and/or the like.

The input interface 110 is configured to receive medical image data 1 of a patient. In the present example, an application of the present invention from the field of Hematology will be described, wherein the medical image data 1 are magnified visual images of blood samples, such as images taken with a microscope after a blood sample has been taken from the patient and has been arranged in a suitable vessel.

Figure 2:
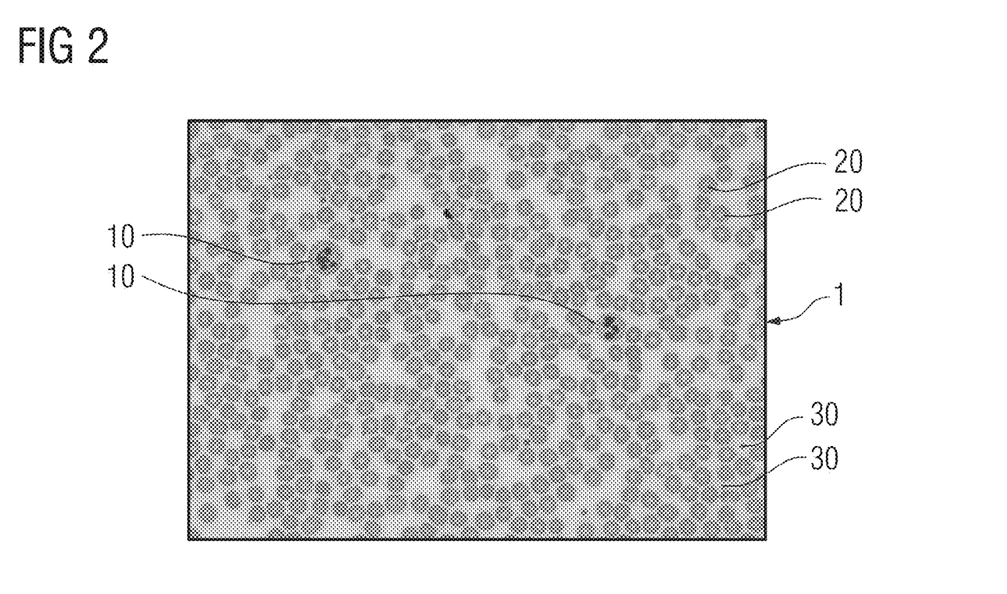
FIG. 2 shows an exemplary magnified visual image of a blood sample.

FIG. 2 shows a magnified visual image of a blood sample as an example for (a part of) medical image data 1. FIG. 2 shows dyed blood cells, i.e., a blood sample to which dye has been applied before its visual scan. However, as has been described in the foregoing, blood samples may alternatively or additionally also be scanned before they are dyed, if they are dyed at all. Grayscale images of dyed and/or undyed images are also possible.

In FIG. 2, two white blood cells 10 are visible as well as a large number of red blood cells 20 and a few platelets 30, not all of which are labelled. It is immediately evident that even obtaining all possible information from this one image involves substantial effort for a human physician. If an analysis or diagnosis involves cross-references or interactions between all objects (blood cells) shown in FIG. 2, this scope already exceeds the physical limitations of a human.

By contrast, FIG. 2 may illustrate only a very small part of the actual visual image (medical image data 1) which may comprise more than 50, more than 100, more than 200, more than 500, or even more than 1000 individual blood cells. In the present example, each blood cell is a part of interest, POI, or, more specifically, an object of interest, OOI.

The medical diagnosis assistance system 100 further comprises a computing device 150 (a PC, a server, a terminal, a cloud computing platform, and the like). The computing device 150 is configured to implement a classification module 151 and an analysis module 152, e.g., by executing a software by a CPU of the computing device 150.

As has been described in the foregoing, the computing device 150 may comprise at least one processing unit such as at least one central processing unit, CPU, and/or at least one graphics processing unit, GPU, and/or at least one field-programmable gate array, FPGA, and/or at least one application-specific integrated circuit, ASIC, and/or any combination of the foregoing. The computing device 150 may further comprise a working memory operatively connected to the at least one processing unit and/or a non-transitory memory operatively connected to the at least one processing unit and/or the working memory. The computing device 150 may be implemented partially and/or completely in a local apparatus and/or partially and/or completely in a remote system such as by a cloud computing platform.

The computing device 150 may optionally comprise a pre-processing module 149 configured to pre-process the medical image data 1 received from the input interface 110. The pre-processing module 149 may be provided for the case wherein the medical image data 1 are not captured in a single data set/sequence which contains the full information needed for assessing the medical problem. For such cases, the pre-processing module 149 may be configured to add, merge, and/or stick individual data sets and/or sequences to form a larger image composed of a number of sub-images added, merged, and/or stitched seamlessly together, preferably without any overlaying texture from the pre-processing. Pre-processing by the pre-processing module 149 may also contain scaling or normalizing of images in pixel-intensity reading or color balancing or in the physical dimension (size, rotation, distortion).

Thus, the medical image data 1 may be provided to the classification module 151 directly by the input interface 110, or the medical image data 1 may be provided to the classification module 151 after pre-processing by the pre-processing module 149. In other words, the pre-processing module 149 may be bypassed, or may simply forward the received medical image data 1, when the medical image data 1 received by the input interface 110 are in a form suitable for the classification module 151 such as a single image file, or a time series, or the like.

The classification module 151 is configured to classify parts of interest, POI, comprising objects of interest, OOI, and/or regions of interest, ROI, within the received medical image data 1, and to assign a corresponding reliability metric to each of the classified POI. In the present example, the classification module 151 is configured to classify the blood components 10, 20, 30.

In this embodiment, the classification module 151 is configured to implement a classifying artificial intelligence entity, CAIE, specifically an artificial neural network, ANN, which is trained and configured to receive at least a portion of the received medical image data 1 and to generate, based thereon, a classifying artificial intelligence entity, CAIE, output classifying the blood components and/or the corresponding reliability metric. The received portion may be significantly larger, i.e., comprise significantly more individual blood components, as shown in FIG. 2.

Furthermore, the classifying artificial intelligence entity, CAIE, comprises a first-level classifying artificial intelligence sub-entity, FLCAISE, and a second-level artificial intelligence sub-entity, SLCAISE, which in this embodiment are both realized as artificial neural networks, ANN, as well.

The first-level classifying artificial intelligence sub-entity, FLCAISE, is trained and configured to receive, as its input, at least a portion (preferably the entirety) of the received medical image data 1 (here: a magnified visual image of the blood sample) and to generate, based thereon, a first-level classifying artificial intelligence sub-entity, FLCAISE, output classifying all of the blood components according to a broad classification scheme, i.e., into blood component types (e.g.: white blood cell; red blood cell; platelet; unknown/rest).

The classification module 151 further comprises a cropping sub-module, CSM, configured to receive the FLCAISE output and to generate excerpts from the received medical image data 1, in particular, by generating equally sized images for each of the blood components 10, 20, 30, each image comprising the corresponding blood component 10, 20, 30 at its center, and a surrounding area defined by the pre-set size of the images. These images, or excerpts, are then provided to the second-level artificial intelligence sub-entity, SLCAISE, as its input.

Figure 3:
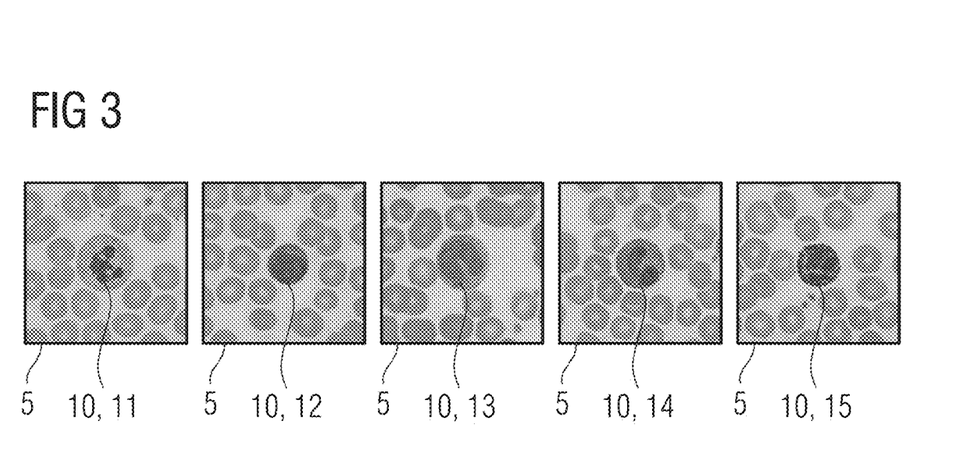
FIG. 3 illustrates several excerpts from a magnified visual image such as that of FIG. 2.

FIG. 3 shows five exemplary excerpts created by the cropping sub-module.

The second-level artificial intelligence sub-entity, SLCAISE, is trained and configured to receive, as its input, the excerpts from the cropping sub-module and the FLCAISE output itself, and to further classify the blood components according to a refined classification scheme. In this refined classification scheme, each blood component type is further classified along one blood component sub-type for each blood component type that comprises blood component sub-types. For blood component types that do not comprise blood component sub-types, the type may be considered its own (and single) sub-type.

In the examples shown in FIG. 3, the central blood component (object of interest, OOI) in each excerpt, respectively, from left to right is classified into the following blood component sub-types: a neutrophile granulocyte 11, a lymphocyte 12, a monocyte 13, an eosinophile granulocyte 14, and a basophile granulocyte 15.

The reliability metric generated by the classification module 151 may be a probability percentage. A single part of interest, POI, may be assigned several reliability metrics, each according to a probability percentage associated with a certain blood component type or blood component sub-type. Usually, the classification into the broad classification scheme, i.e., into blood component types, is so reliable that preferably the reliability metric indicates the probability percentage for at least one blood component sub-type.

The analysis module 152 is configured to determine, based on the part of interest, POI, (here: blood components 10, 20, 30) and the assigned reliability metric, an analysis of the medical image data 1. As has been described in the foregoing, the presence of an Auer rod as one blood component may be indicative for acute leukemia (ALM), so the analysis in that case may comprise a diagnosis of acute leukemia or an assistance signal indicating that acute leukemia may be present and/or the like.

The analysis module 152 may take the reliability metric into account by basing the analysis only on the top percentile (e.g., 10%, 20%, 30% or the like) of reliable classifications according to the reliability metric. In other words, only the most trusted classifications are used as a basis for the analysis.

For example, blood cell classification cannot always be performed with high accuracy for every single cell, because abnormal cells do not always follow the morphologic criteria of a respective class of blood cells. Therefore, another strength of the present approach lies in the fact that the analysis preferably will be done on the most trusted blood cell classifications of input data and by omitting less accurate classifications which would introduce some additional uncertainty into the analysis or diagnosis. This approach is quite comparable to what is done by humans in diagnosing samples.

The output of the classification module 151 is preferably scanned, structured, and/or sorted, by the analysis module 152, according to the reliability metric of the classification and the classification itself. Based on all the classified parts of interest, POI, with a reliability metric exceeding a predefined value, an analysis, in particular a medical diagnosis, gets inferred from an artificial intelligence entity such as an AI network or a computer algorithm either trained from other datasets as training data by supervised, semi-supervised, and/or unsupervised computer learning or based on given rules according to medical procedures or classification, preferably according to standard of care procedures.

As has been described in the foregoing, the analysis module 152 may also provide an analysis reliability value (or: diagnosis reliability value in the case of a diagnosis) which may be determined based on rules or patterns stored in the analysis module 152, e.g., in a database thereof.

Especially in the combination of the reliability metric, and an optionally known diagnosis reliability, the medical diagnosis assistance system 100 may provide a complete diagnosis as its analysis.

In the above-mentioned case of acute leukemia, AML, for example, the presence of Auer rods indicates the presence of AML with certainty (diagnosis reliability 100%, as an example). If the classification includes, or indicates, the presence of an Auer rod in the medical image data with a reliability metric higher than a predefined threshold (e.g., 95%) then a diagnosis of AML may be output by the analysis module 152. The diagnosis (or indication) may also be accompanied by a reliability estimate. In case both percentages are used as the reliability metric and the diagnosis reliability value, a product of the two percentages may be used. For example, the reliability metric for the detection of at least one Auer rod may be determined to be 95%, and the diagnosis reliability from an Auer rod to the diagnosis of leukemia is 100%, then the diagnosis of AML may be output together with a reliability estimate of 100% times 95%=95%.

The output interface 190 is configured to output an output signal 71 indicating the analysis. As depicted in FIG. 1, the output signal 71 may be output to the exterior of the medical diagnosis assistance system 100, e.g., into a cloud storage, a cloud computing platform, or the like. The output signal 71 indicating the analysis may also be provided to a graphical user interface 153 which may be a part of the medical diagnosis assistance system 100 (as illustrated in FIG. 1) or which may be external to it.

The graphical user interface 153 may provide a user, on demand, with the option to quickly review the excerpts, e.g., as shown in the individual parts of FIG. 3, which relate to a specific result of the analysis, specifically, based on which the result of the analysis has been concluded. For example, in the case of AML, the analysis result may be provided by the graphical user interface 153 to the user next to a button labeled "show basis." Touching this button would prompt the graphical user interface 153 to show the user all of the excerpts which show an Auer rod.

The graphical user interface 153 may also provide the user, on demand, with all excerpts together with a corresponding classification (broad and/or refined, i.e., here: blood component type and/or blood component sub-type), and give the user the option to re-classify the blood component with which each excerpt is associated (i.e., which is shown in its center). For example, the graphical user interface 153 may, on demand, show a drop-down menu for each excerpt, the drop-down menu comprising a list of all possible classifications. The list may be sorted according to the reliability metric (i.e., percentage of confidence) and/or the classification chosen by the classification module 151 may be highlighted in some manner. The user may then be able to manually select another classification, thus changing the classification of the blood component in that excerpt.

Since some classes are more stable classified by the classification module 151, the analysis or diagnosis might be accompanied by the statistical information on the relative population of all available classes. This reference is advantageous since the selection of samples in step 2 according to the trust level of classification in step 1 might most probably change the statistics in the distribution of the population of the classes after step 1. This distribution might also be a valuable input to step 2 in addition to the most prominent/ secured representative samples in each class.

For example, for healthy donors there is a medical norm for the distribution of parts of interest, POI, among the available classifications, and the POIs are usually not evenly distributed. A change in population distribution of the classifications (with respect to the norm) may therefore be an indication towards a specific kind of disease or syndrome. Thus, information of the medical norm for the distribution and the actual distribution according to the classification may be used for generating the diagnosis or analysis.

As has been described in the foregoing, some steps in the described process may be iteratively performed in a so-called refinement loop. Such a loop can be started automatically, or on a specific trigger by the medical diagnosis assistance system 100 (e.g., an ambiguous result of the analysis) and/or by a user. For example, in the above case in which the user re-classifies one or more parts of interest, POI, the user may be asked by the graphical user interface 153 to confirm all changes. After the confirmation is made by the user and at least one change has been made, a refinement loop may automatically commence. In this way, the knowledge expressed by the user in the changes is taken into account for an eventually improved analysis.

For a refinement loop, first a preliminary analysis is generated by the analysis module 152; the classification module 152 re-classifies the POI and/or re-assigns the corresponding reliability metric based on the preliminary analysis, and determines, based on the re-classified POI and/or the re-assigned corresponding reliability metric, another preliminary analysis which in turn may then be used to start another refinement loop or which may, instead, be used after the last refinement loop as the analysis of the analyzing module 152.

As an example for an automatically triggered refinement loop, in the classification step, one object of interest, OOI, may have been classified as "class X" with 40% and "class Y" with 60% such that a classification into "class Y" is performed (i.e., into the class with the higher reliability metric value). The analysis in this example then provides a reliable (i.e., with an analysis reliability above a pre-defined threshold) diagnosis that either disease A or disease B is found, both of which are incompatible with a finding of "class Y."

Then, in the refinement loop, that information is transferred to the analysis module which may then exclude the incompatible class ("class Y" in this example). Thus, the same object of interest, OOI, is then re-classified into "class X," and the new reliability metric may now equal, for example, 75%. The next preliminary analysis within the loop is then based on the new entirety of classifications (after the re-classifying) which may then have a clear preference of the likelihood of disease B over the likelihood of disease A. This iterative process in the refinement loop(s) simulates the thinking of human physicians which evaluate possible analysis results and constantly challenge and re-evaluate their initial assumptions and classifications.

The number n of refinement loops may be pre-set (for example n=1, n=5, etc.), or the performing of a refinement loop may be dependent on a particular analysis result (e.g., likelihood of two different diagnoses differing by less than z %, for example, z=20, or z=10, or z=5).

A refinement loop may also be triggered by a user in other ways. For example, the preliminary diagnosis may be generated by the analysis module 152 based on a user input. For instance, a first analysis generated automatically by the classification module may be displayed to the user in the graphical user interface 153, offering at least one alternative analysis result (or diagnosis result), each with a corresponding analysis probability.

The user, a physician, biologist, or the like, may then assess the first analysis, review the corresponding medical image data 1, and so on, and may be able to dismiss one or more of the alternatives offered in the first analysis, for example, by selecting a "dismiss this alternative" function in the graphical user interface. Based on this user input, the analysis module generates a second analysis, being the previously mentioned "preliminary analysis" that goes into the refinement loop. After the loop, the user may be provided with new alternatives via the graphical user interface 153, and so on. A stopping condition for breaking out of the refinement loops may be when the user indicates satisfaction (or agreement) with one or more alternatives or when only one alternative is left, and/or when no condition for automatically commencing another refinement loop is triggered.

In some variants, the result of all refinement loops is presented to the user by the graphical user interface 153, in other variants the user may be given the opportunity to select, or trigger, after each refinement loop anew whether another refinement loop is to be performed or not. In any case, the result of the final refinement loop may be displayed by the graphical user interface 153 and/or be coded into an output signal 71 by the output interface 190. The output signal 71 can be directed and configured to start a workflow, control a medical device, deposit data in a database, create a human-readable output or printout, and/or the like.

Figure 4:
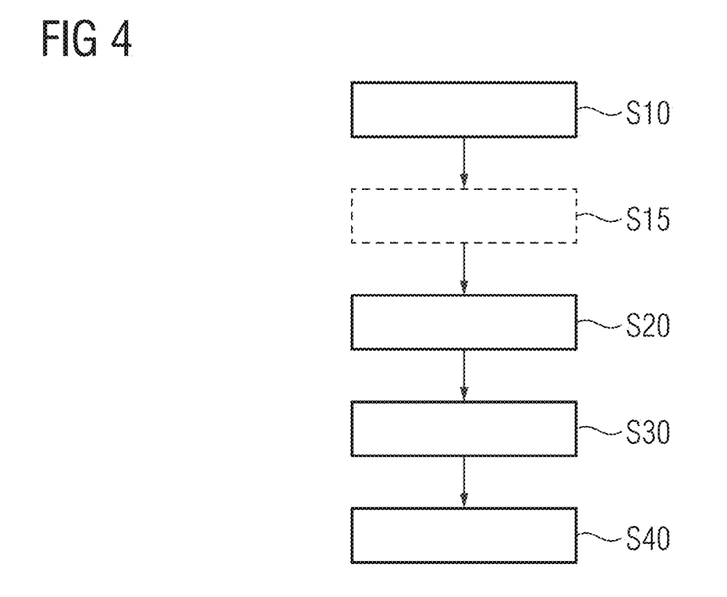
FIG. 4 shows a flow diagram schematically illustrating a computer-implemented medical diagnosis assistance method according to another embodiment of the present invention.

FIG. 4 shows a flow diagram schematically illustrating a computer-implemented medical diagnosis assistance method according to an embodiment of the present invention. It shall be understood that the method according to the present invention may be performed by the medical diagnosis assistance system 100 according to the present invention. Therefore, any embodiment of the method according to the present invention may be adapted, modified, or refined according to any of the variants, options, modifications, or refinements of any of the embodiments of the medical diagnosis assistance system 100 according to the present invention, in particular as has been described with respect to FIG. 1 through FIG. 3. For this reason, the method steps will only be briefly described, and a reference to the detailed foregoing description, both in general and referring to the drawings, is implied.

One or more method steps may be performed at the same time, in an integrated way, or separately from one another. The numbering of the method steps does not necessarily imply a time order of steps.

In a step S10, medical image data 1 of a patient is received, e.g., as has been described in the foregoing with respect to the input interface 110.

In an optional step S15, the medical image data 1 may be pre-processed as has been described with respect to the pre-processing module 149 in the foregoing.

In a step S20, parts of interest, POI, comprising objects of interest, OOI, and/or regions of interest, ROI, within the received medical image data 1 are classified, in particular as has been described in the foregoing with respect to the classification module 151.

In a step S30, a corresponding reliability metric is assigned to each of the classified part of interest, POI, advantageously again as has been described in the foregoing with respect to the classification module 151.

In a step S40, an analysis of the medical image data 1 is determined based on the POI and the assigned reliability metric, in particular, as has been described in the foregoing with respect to the analysis module 152.

One or more refinement loops as described in the foregoing may be performed, in particular, by repeating step S20, step S30, and/or step S40.

In some advantageous variants, the method may comprise one or more of the steps which have already been implicitly described in more detail in connection with the medical diagnosis assistance system 100.

Specifically, the method may comprise steps of:
generating, using a trained first-level classifying artificial intelligence sub-entity, FLCAISE, a FLCAISE output classifying at least a part of the part of interest, POI, according to a broad classification scheme, based on at least a portion of the received medical image data 1; and generating, using a trained second-level classifying artificial intelligence sub-entity, SLCAISE, a SLCAISE output classifying the at least part of the part of interest, POI, according to a refined classification scheme, based on at least a portion of the received medical image data 1 and on the first-level classifying artificial intelligence sub-entity, FLCAISE, output.

Similarly, the method may comprise steps of:
generating excerpts 5 from the received medical image data 1, each excerpt 5 associated with a single POI and comprising at least the corresponding associated POI, and providing the generated excerpts to the second-level artificial intelligence sub-entity, SLCAISE, as the input of the second-level artificial intelligence sub-entity, SLCAISE.

Figure 5:
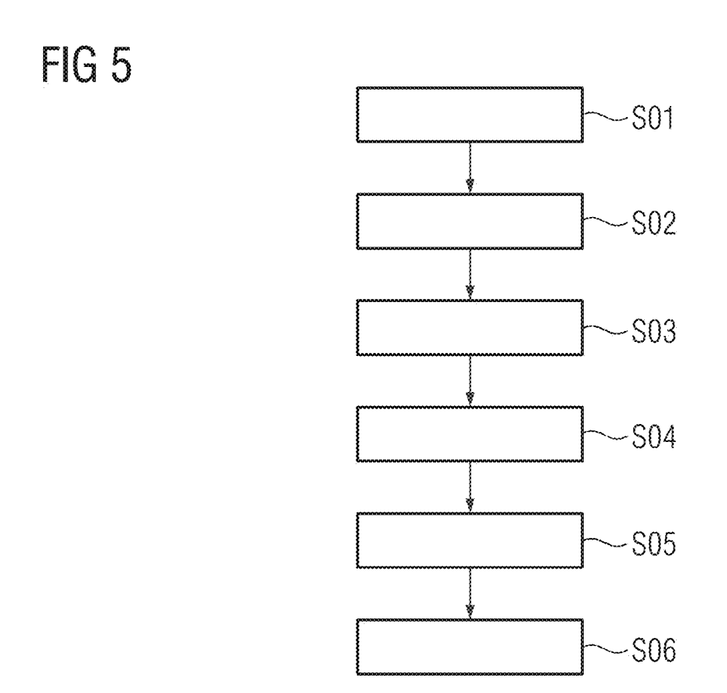
FIG. 5 shows a flow diagram schematically illustrating a computer-implemented method for training an artificial intelligence entity according to yet another embodiment of the present invention.

FIG. 5 shows a flow diagram illustrating a training method for training a classifying artificial intelligence entity, CAIE, according to another embodiment of the present invention.

In a step S01, first labelled samples of medical image data 1 are provided. For example, each sample may consist of, or comprise, an image as shown in FIG. 2, wherein for each blood component, or part of interest, POI, a classification into a blood component type is provided as a label. The label may comprise additional data such as data defining a bounding box about each part of interest, POI. The labelled samples may be produced by a physician or biologist labelling the part of interest, POI, shown in the image. As has been described in the foregoing, sample sets with dyed and/or undyed images may be used, either simultaneously or sequentially.

In a step S02, a first-level classifying artificial intelligence sub-entity, FLCAISE, is provided in a preliminary state, e.g., with randomized initial values for an artificial neural network, ANN, especially a convolutional neural network, CNN.

In a step S03, supervised learning is performed, using the first labelled samples, in order to train the first-level classifying artificial intelligence sub-entity, FLCAISE, to classify parts of interest, POI, within an input of the first-level classifying artificial intelligence sub-entity, FLCAISE, according to a broad classification scheme.

In a step S04, second labelled samples of medical image data 1 are provided. For example, each sample may consist of, or comprise, an image as shown in any of the excerpts 5 of FIG. 3, wherein for each blood component, or part of interest, POI, in the center of the excerpt 5 a classification into a blood component sub-type is provided as a label. The label may comprise additional data such as data defining a bounding box about each part of interest, POI. The labelled samples may be produced by a physician or biologist labelling the part of interest, POI, shown in the image. As has been described in the foregoing, sample sets with dyed and/or undyed images may be used, either simultaneously or sequentially.

In a step S05, a second-level artificial intelligence sub-entity, SLCAISE, is provided in a preliminary state, e.g., with randomized initial values for an artificial neural network, ANN, especially a convolutional neural network, CNN.

In a step S06, supervised learning is performed, using the second labelled samples, in order to train second-level artificial intelligence sub-entity, SLCAISE, to classify parts of interest, POI, within an input of the second-level classifying artificial intelligence sub-entity, SLCAISE, according to a refined classification scheme.

In a step S07, a trained classifying artificial intelligence entity, CAIE, is provided which comprises both the trained first-level classifying artificial intelligence sub-entity, FLCAISE, and the trained second-level artificial intelligence sub-entity, SLCAISE.

Figure 6:
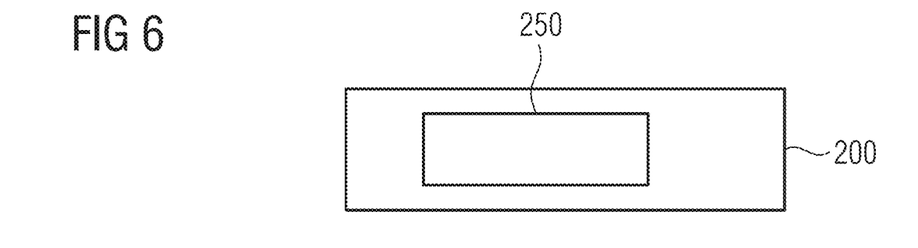
FIG. 6 shows a block diagram illustrating a computer program product according to yet another embodiment according to the present invention.

FIG. 6 shows a schematic block diagram illustrating a computer program 200 product according to another embodiment of the present invention. The computer program product 200 comprises executable program code 250 configured to, when executed, perform the method according to any embodiment of the present invention, in particular the method as explained with respect to FIG. 4 and/or the method as explained with respect to FIG. 5.

Figure 7:
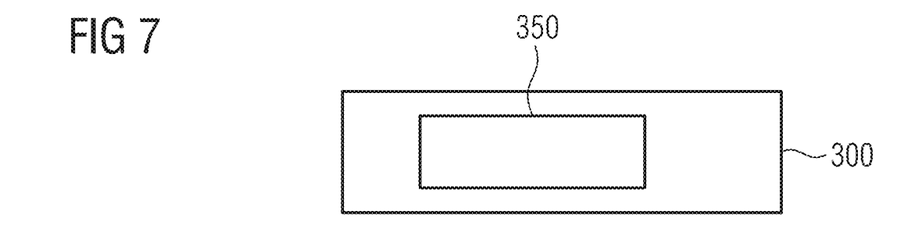
FIG. 7 shows a block diagram illustrating a data storage medium according to still another embodiment according to the present invention.

FIG. 7 shows a schematic block diagram illustrating a computer-readable, non-transitory data storage medium 300 product according to another embodiment of the present invention. The data storage medium 300 comprises executable program code 350 configured to, when executed, perform the method according to any embodiment of the present invention, in particular the method as explained with respect to FIG. 4 and/or the method as explained with respect to FIG. 5.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

The embodiments were chosen and described in order to best explain the principles of the invention and its practical applications, to thereby enable others skilled in the art to best utilize the invention and various embodiments with various modifications as are suited to the particular use contemplated.

LIST OF REFERENCE SIGNS

1 medical image data
5 excerpt 10 white blood cell
11-15 white blood cell sub-types
20 red blood cells
30 platelets
71 output signal
100 medical diagnosis assistance system
110 input interface
149 pre-processing module
150 computing device
151 classifying module
152 analysing module
153 graphical user interface
190 output interface
200 computer program product
250 program code
300 data storage medium
350 program code
S01-S06 method steps
S10-S40 method steps

The invention claimed is:

1. A medical diagnosis assistance system, comprising:
an input interface configured to receive medical image data of a patient;
a computing device configured to implement:
a classification module configured to classify parts of interest, POI, comprising objects of interest, OOI, or regions of interest, ROI, within the received medical image data, and to assign a corresponding reliability metric to each of the classified POI; wherein:
the classification module is configured to implement a classifying artificial intelligence entity, CAIE, which is trained and configured to receive at least a portion of the received medical image data and to generate, based thereon, a CAIE output classifying the POI or the corresponding reliability metric,
the CAIE comprises a first-level classifying artificial intelligence sub-entity, FLCAISE, and a second-level artificial intelligence sub-entity, SLCAISE,
the FLCAISE is trained and configured to receive, as its input, at least a portion of the received medical image data and to generate, based thereon, a FLCAISE output classifying at least a part of the POI according to a broad classification scheme; and
the SLCAISE is trained and configured to receive, as its input, at least a portion of the received medical image data and the FLCAISE output, and to further classify at least the part of the POI according to a refined classification scheme, and
an analysis module configured to determine, based on the POI and the assigned reliability metric, an analysis of the medical image data; and
an output interface configured to output an output signal indicating the analysis.

2. The medical diagnosis assistance system of claim 1, wherein the classification module comprises a cropping sub-module, CSM, configured to receive the FLCAISE output and to generate excerpts from the received medical image data, each excerpt associated with a single POI and comprising at least the corresponding associated POI, and to provide the generated excerpts to the SLCAISE as the input of the SLCAISE.

3. The medical diagnosis assistance system according to claim 1, wherein the analysis module is configured to implement an analyzing artificial intelligence entity, AAIE, which is trained and configured to receive, as its input, the classified POI and the assigned reliability metric and to generate, based thereon, the analysis.

4. The medical diagnosis assistance system according to claim 1,
wherein the classification module and the analysis module are configured to perform at least one refinement loop comprising:
generating, by the analysis module, a preliminary analysis;
receiving, by the classification module, the preliminary analysis by the analysis module and re-classifying the POI or re-assigning the corresponding reliability metric based on the preliminary analysis, and
determining, based on the re-classified POI or the re-assigned corresponding reliability metric, another preliminary analysis; and
wherein after the last refinement loop the preliminary analysis is used as the analysis of the analyzing module.

5. The medical diagnosis assistance system according to claim 1, wherein the input interface is configured to receive medical image data comprising at least 20 parts of interest, POI, to be classified, and wherein the classification module is configured to classify at least 20 of the at least 20 parts of interest, POI, comprised in the medical image data.

6. The medical diagnosis assistance system according to claim 1, wherein the medical image data are magnified visual images of blood samples, and wherein the parts of interest, POI, comprise blood components within the blood samples as objects of interest, OOI.

7. A computer-implemented medical diagnosis assistance method, comprising:
receiving medical image data of a patient;
classifying parts of interest, POI, comprising objects of interest, OOI, or regions of interest, ROI, within the received medical image data via a classifying artificial intelligence entity, CAIE, which is trained and configured to receive at least a portion of the received medical image data and to generate, based thereon, a CAIE output classifying the POI or the corresponding reliability metric, wherein:
the CAIE comprises a first-level classifying artificial intelligence sub-entity, FLCAISE, and a second-level artificial intelligence sub-entity, SLCAISE,
the FLCAISE is trained and configured to receive, as its input, at least a portion of the received medical image data and to generate, based thereon, a FLCAISE output classifying at least a part of the POI according to a broad classification scheme; and
the SLCAISE is trained and configured to receive, as its input, at least a portion of the received medical image data and the FLCAISE output, and to further classify at least the part of the POI according to a refined classification scheme,
assigning a corresponding reliability metric to each of the classified POI; and
determining, based on the POI and the assigned reliability metric, an analysis of the medical image data.

8. The method of claim 7, further comprising steps of:
generating, using the FLCAISE, a FLCAISE output classifying at least a part of the POI according to a broad classification scheme, based on at least a portion of the received medical image data; and
generating, using the SLCAISE, a SLCAISE output classifying the at least part of the POI according to a refined classification scheme, based on at least a portion of the received medical image data and on the FLCAISE output.

9. The method of claim 8, further comprising steps of:
generating excerpts from the received medical image data, each excerpt associated with a single POI and comprising at least the corresponding associated POI, and
providing the generated excerpts to the SLCAISE as the input of the SLCAISE.

10. A computer-implemented training method for training a classifying artificial intelligence entity, CAIE, to receive at least a portion of received medical image data and to generate, based thereon, a CAIE output classifying parts of interest, POI, comprising objects of interest, OOI, or regions of interest, ROI, within the received medical image data, or a corresponding reliability metric, the method comprising steps of:
providing first labelled samples of medical image data;
providing a first-level classifying artificial intelligence sub-entity, FLCAISE, in a preliminary state;
performing supervised learning, using the first labelled samples, in order to train the first-level classifying artificial intelligence sub-entity, FLCAISE, to generate a FLCAISE output classifying parts of interest, POI, within an input of the first-level classifying artificial intelligence sub-entity, FLCAISE, according to a broad classification scheme;
providing second labelled samples of medical image data;
providing a second-level artificial intelligence sub-entity, SLCAISE, in a preliminary state;
performing supervised learning, using the second labelled samples and the FLCAISE output, in order to train the second-level artificial intelligence sub-entity, SLCAISE, to further classify parts of interest, POI, within an input of the second-level classifying artificial intelligence sub-entity, SLCAISE, according to a refined classification scheme; and
providing a trained classifying artificial intelligence entity, CAIE, comprising both the trained first-level classifying artificial intelligence sub-entity, FLCAISE, and the trained second-level artificial intelligence sub-entity, SLCAISE.

11. The method of claim 10, wherein the second labelled samples comprise less parts of interest, POI, than the first labelled samples.

12. The method of claim 10,
wherein the first labelled samples comprise magnified visual images of blood samples wherein blood components, as objects of interest, OOI, are labelled according to blood component types, and
wherein the second labelled samples comprise magnified visual images of blood samples wherein blood components, as objects of interest, OOI, are labelled according to blood component sub-types.

13. The method of claim 10, wherein the first labelled samples or the second labelled samples comprise magnified visual images of undyed or dyed blood samples.

* * * * *